US00PP21878P2

(12) United States Plant Patent
Verschoor

(10) Patent No.: US PP21,878 P2
(45) Date of Patent: Apr. 19, 2011

(54) *PHLOX* PLANT NAMED 'JADE'

(50) Latin Name: *Phlox paniculata*
Varietal Denomination: Jade

(76) Inventor: Jan Verschoor, Haarlem (NL)

( * ) Notice: Subject to any disclaimer, the term of this patent is extended or adjusted under 35 U.S.C. 154(b) by 9 days.

(21) Appl. No.: 12/590,916

(22) Filed: Nov. 16, 2009

(51) Int. Cl.
*A01H 5/00* (2006.01)

(52) U.S. Cl. ..... Plt./320

(58) Field of Classification Search ..... Plt./320
See application file for complete search history.

(56) References Cited

U.S. PATENT DOCUMENTS

PP18,196 P2 * 11/2007 Verschoor ..... Plt./320
PP19,600 P2 * 12/2008 Verschoor ..... Plt./320
PP19,968 P2 * 4/2009 Verschoor ..... Plt./320
PP20,189 P2 * 7/2009 Geerlings ..... Plt./320

* cited by examiner

*Primary Examiner* — Wendy Haas
(74) *Attorney, Agent, or Firm* — Penny J. Aguirre

(57) ABSTRACT

A new cultivar of *Phlox,* 'Jade', characterized by its large flowers that are pure white in color with green tips at apex of each petal, its healthy foliage with a high degree of mildew resistance, and its compact plant habit with sturdy stems.

2 Drawing Sheets

Botanical classification: *Phlox paniculata.*
Cultivar designation: 'Jade'.

BACKGROUND OF THE INVENTION

The present invention relates to a new and distinct cultivar of *Phlox* plant, botanically known as *Phlox paniculata* 'Jade' and will be referred to hereafter by its cultivar name, 'Jade'. The new cultivar represents a new herbaceous perennial grown for landscape use.

The Inventor selected the new cultivar as a single unique plant in a trial plot in Haarlem, The Netherlands in summer of 2007. 'Jade' was selected from the results of an open pollination of unnamed proprietary plants of *Phlox paniculata* and the parentage is unknown.

Asexual reproduction of the new cultivar was first accomplished by stem cuttings in Haarlem, The Netherlands in summer of 2007 by the Inventor. It has been determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Jade' from other varieties of *Phlox* known to the Inventor.

1. 'Jade' exhibits flowers that are pure white in color with green tips at apex of each petal.
2. 'Jade' exhibits large flowers that are up to 2 cm in diameter.
3. 'Jade' exhibits healthy foliage with a high degree of mildew resistance.
4. 'Jade' exhibits a compact plant habit with sturdy stems.

The closest comparison plant to 'Jade' is 'White Admiral' (not patented), which is similar to 'Jade' in having flowers that are white in color. 'White Admiral' differs from 'Jade' in being less compact, in having smaller flowers that lack green colored tips on the petals, in having a less compact habit, and in having weaker stems. 'Jade' can also be compared to the cultivars 'David' (not patented) and 'Pina Colada' (U.S. Plant Pat. No. 19,968). 'David' and 'Pina Colada' are similar to 'Jade' in having mildew resistant foliage and flowers that are pure white in color, however 'David' and 'Pina Colada' differ from 'Jade' in lacking green colored tips on the flower petals.

BRIEF DESCRIPTION OF THE DRAWING

The accompanying colored photographs illustrate the overall appearance and distinct characteristics of the new *Phlox.* The photographs were taken of a one year-old plant of 'Jade' as grown a trial garden in a garden in Haarlem, The Netherlands.

The photograph in FIG. 1 is a view of a plant of 'Jade' in bloom.

Figure 1:
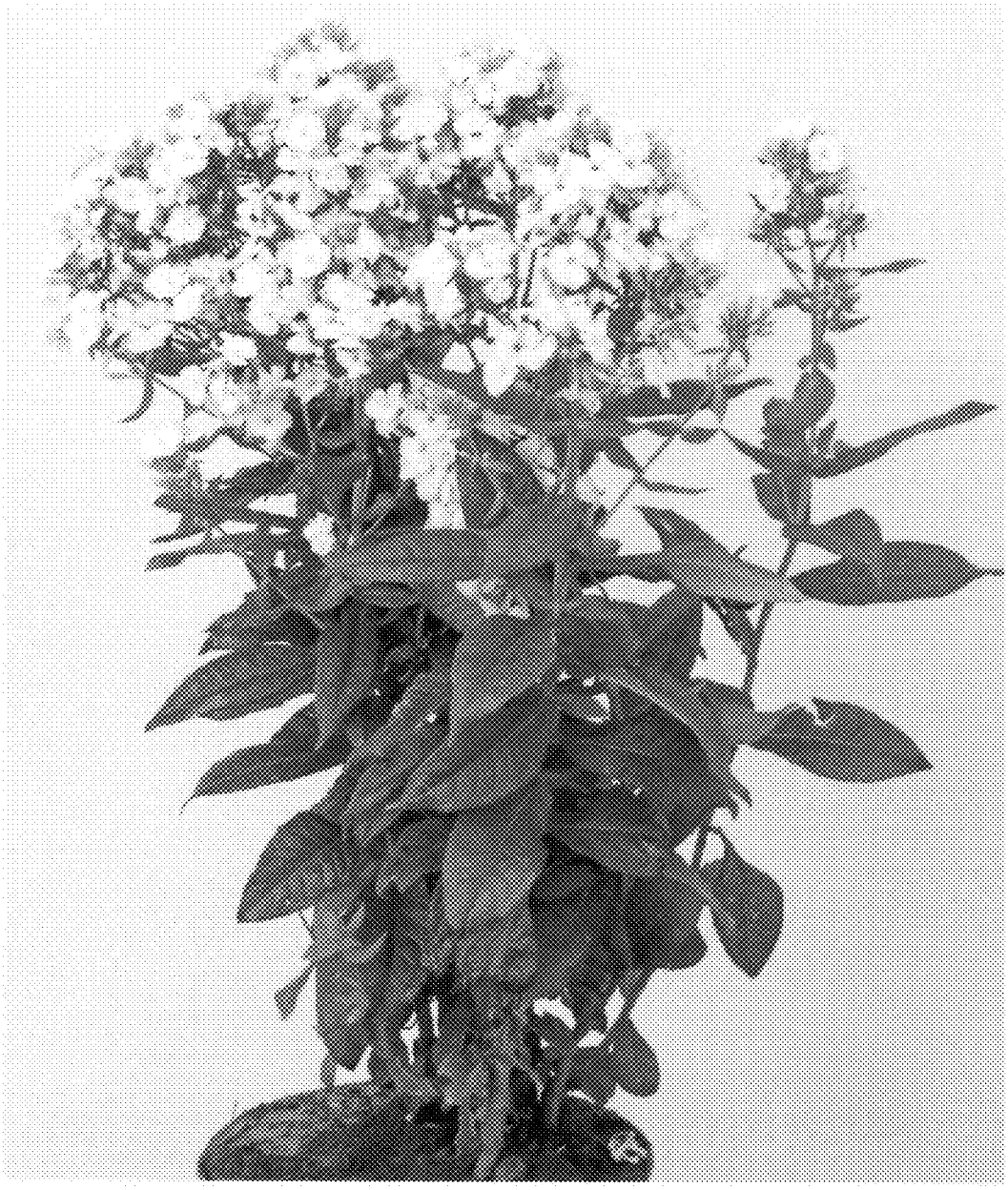
Figure 2:
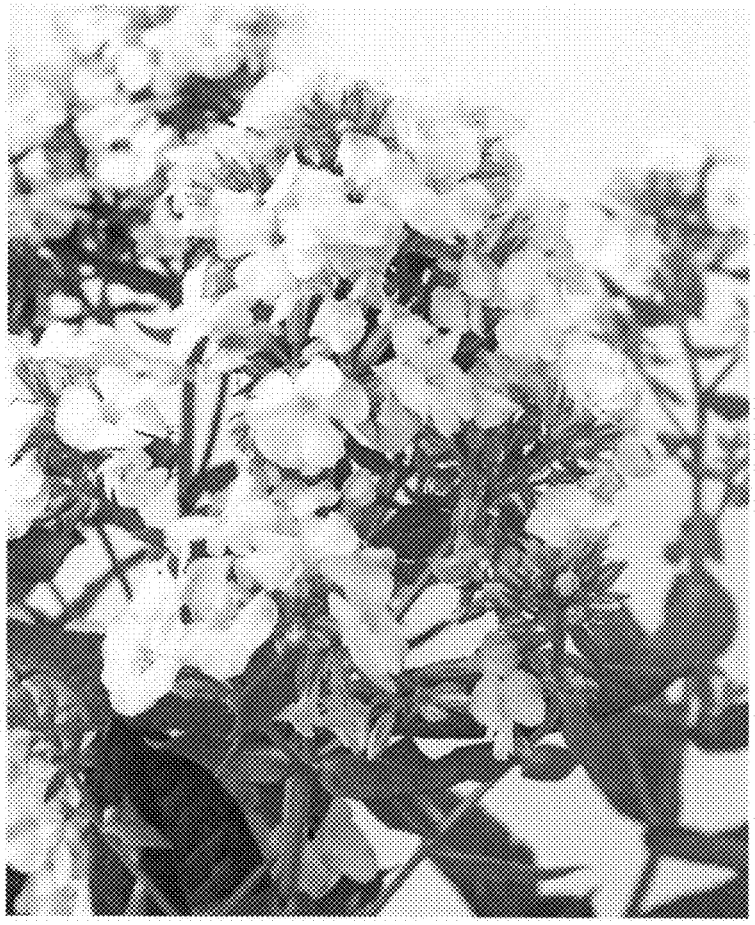

The photograph in FIG. 2 is a close-up view of an inflorescence of 'Jade'.

Figure 3:
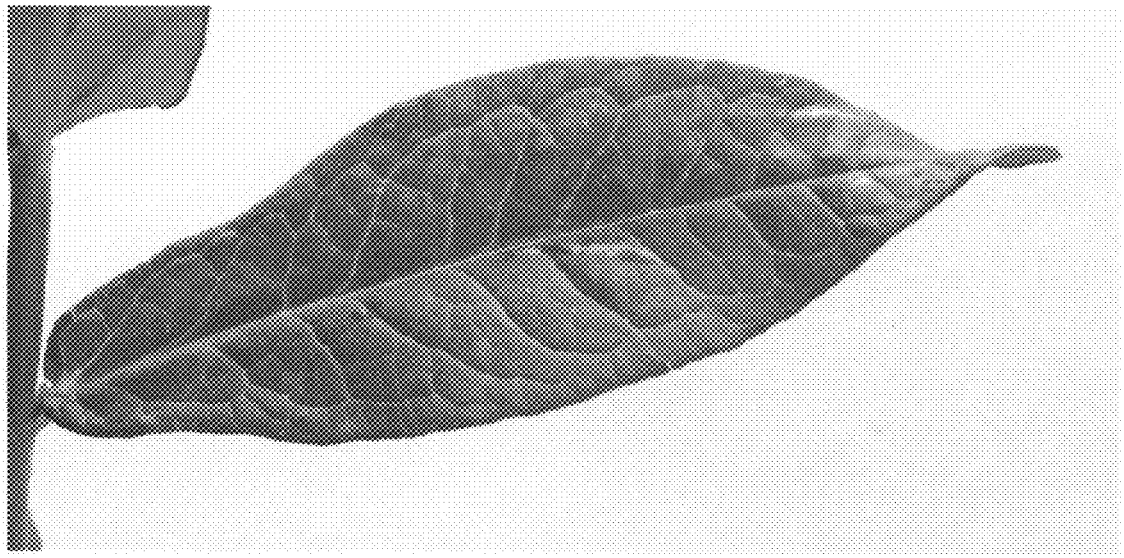

The Photograph in FIG. 3 provides a close-up view of a leaf of 'Jade'. The colors in the photograph may differ slightly from the color values cited in the detailed botanical description, which accurately describe the colors of the new *Phlox.*

DETAILED BOTANICAL DESCRIPTION OF THE PLANT

The following is a detailed description of one year-old plants of the new cultivar as grown outdoors in a trial plot in Haarlem, The Netherlands. The plants were grown under average day temperatures of 15° C. to 32° C. and average night temperatures of 8° C. to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Mid to late summer in the Netherlands.

*Plant habit.*—Herbaceous perennial, compact, upright.

*Height and spread.*—Reaches about 55.5 cm in height and about 39.8 cm in spread.

*Cold hardiness.*—At least in U.S.D.A. Zone 4.

*Diseases and pests.*—Has shown good resistance to powdery mildew.

*Root description.*—Fibrous.

Growth and propagation:

*Growth rate.*—Moderate.

*Propagation.*—Stem cuttings, division also possible.

Stem description:

*Stem size.*—An average of 36.5 cm in length and 5 mm in width.

*Stem shape.*—Round.

*Stem strength.*—Strong and sturdy.

*Stem color.*—144A.

*Stem surface.*—Glabrous, slightly glossy.

*Stem aspect.*—Held nearly upright.

*Internode length.*—An average of 3.2 cm.

*Branching habit.*—Flowering stems emerge from crown, an average of 8 stems per plant one year in age, no lateral branches.

Foliage description:

*Leaf shape.*—Narrowly elliptic to narrowly obovate.

*Leaf division.*—Simple.

*Leaf base.*—Truncate.

*Leaf apex.*—Narrowly acute.

*Leaf venation.*—Pinnate, not conspicuous, 144C on upper surface and 144C to 144D on lower surface.

*Leaf margins.*—Slightly revolute, very finely serrate (about 30 serrations per cm).

*Leaf attachment.*—Petiolate.

*Leaf arrangement.*—Opposite.

*Leaf surface.*—Smooth and glabrous on upper and lower surface.

*Leaf color.*—Upper surface newly formed; 143B, lower surface newly formed; 138B, upper surface mature; N137C, lower surface mature; 138B.

*Leaf size.*—An average of 9.2 cm in length and 3.5 cm in width.

*Leaf quantity.*—An average of 22 per stem.

*Leaf fragrance.*—None.

*Petioles.*—V-shaped, an average of 4 mm in width and 3 mm in length, 144C in color, surface is glabrous.

Flower description:

*Inflorescence type.*—Compound terminal panicle.

*Lastingness of inflorescence.*—About 3 to 4 weeks from the opening of the first flower to senescence of last flower, individual flower lasts about 10 days.

*Inflorescence size.*—An average of 19.6 cm in height and 16.2 cm in diameter.

*Flower fragrance.*—Faint to moderate, sweet *phlox* fragrance.

*Flower number.*—Average of 200 per inflorescence, one inflorescence per flowering stem.

*Flower aspect.*—Upright to outward, dependant on location of the inflorescence.

*Flower bud.*—An average of 1.2 cm in length and up to 4.5 mm in width, oblanceolate in shape, 150C and 150D in color with calyx portion 148B and 148D.

*Flower form.*—Explanate with tubular base.

*Flower size.*—An average of 2.1 cm in length and 1.6 cm in width.

*Corolla tube.*—About 1.2 cm in length, 3 mm in width, color 157C to 157D on outer and inner surface, dull and smooth surface.

*Corolla lobes.*—5, orbicular in shape, held horizontally when fully open, slightly overlapping, about 1 cm in length and width, apex rounded, base fused to tube, entire margins, upper surface color when opening; 155C to 157D with apex 150B to 150C, lower surface color when opening; 155C to 157D, upper surface color when fully open; 155C to 157C with apex 150B to 150C, lower surface color when fully open; 155C to 155D with apex 150B to 150C, non-fading, surface is dull and smooth on upper and lower surface.

*Calyx.*—Campanulate in form, comprised of fused sepals with sepal tips free, an average of 8 mm in length and 8 mm in width.

*Sepals.*—5, primarily fused with free tips, linear in shape, margins entire, base fused (about 25%), apex narrowly apiculate, an average of 8 mm in length and 2 mm in width, surface is smooth and moderately glossy, color of newly open flowers upper and lower surface; 144B with margins 144D, color of fully open flowers upper and lower surface; 144B with margins 144D.

*Peduncles.*—Oval in shape, strong, primary an average of 16.4 cm in length and 3.5 mm in width, secondary an average of 7.4 cm in length and 1.5 mm in width, primary held upright, secondary held at about a 30° angle, glabrous surface, color 144B to 144C.

*Pedicels.*—Oval in shape, strong, an average of 4 mm in length and 1 mm in width, glabrous surface, color 144C.

Reproductive organs:

*Gynoecium.*—1 pistil, stigma has 3 branches about 6 mm in length and 145C in color, style is about 5 mm in length and 145C in color, ovary is inferior and 143A in color.

*Androcoecium.*—5 stamens, anthers are basifixed, oblong in shape, 1.5 mm in length and 158A to 158B in color, filaments are adnate to petals and 1 mm in length, pollen is low in quantity and ranges from 11C to 11D in color.

*Seeds.*—None observed.

It is claimed:

1. A new and distinct cultivar of *Phlox* plant named 'Jade' as herein illustrated and described.

* * * * *